United States Patent [19]

Branner-Jorgensen

[11] 4,255,454
[45] Mar. 10, 1981

[54] THERMAL DESTABILIZATION OF MICROBIAL RENNET

[75] Inventor: Sven Branner-Jorgensen, 24 Johannevej, DK-2920 Charlottenlund, Denmark

[73] Assignee: Sven Branner-Jorgensen, Charlottenlund, Denmark

[21] Appl. No.: 973,937

[22] Filed: Dec. 28, 1978

[51] Int. Cl.$^3$ .................... A23C 19/02; A23C 21/00; C12N 9/58
[52] U.S. Cl. ........................ 426/36; 426/63; 426/583; 426/801; 435/184; 435/223
[58] Field of Search .............. 426/36, 63, 583, 801; 435/184, 223

[56] References Cited

U.S. PATENT DOCUMENTS 3,549,390   12/1970   Charles et al. ................. 426/36

OTHER PUBLICATIONS

Ilany et al., Milk-Clotting Activity of Proteolytic Enzymes, J. DC., Sci., vol. 52, No. 1, 1969 (pp. 43-46).
Vratsanos, S. M., On the Mechanism of Enzyme Action, LXXI Acylations of Trypsin in Organic Solvents, Archives of Biochem. & Biophys. vol. 90, 1960 (pp. 132-138).
Richert, W. S., Structural and Functional Determinants of *Mucor Miehei* Protease, Biochim et Biophys. Acta., vol. 271, 1972 (pp. 93-101).

*Primary Examiner*—David M. Naff
*Attorney, Agent, or Firm*—Fidelman, Wolffe & Waldron

[57] ABSTRACT

Microbial rennet having reduced thermal stability is produced by acylating the rennet with a monocarboxylic acid acyl radial of between 1 and 6 carbon atoms. Making cheese with the microbial rennet having reduced thermal stability enables the production of pasteurized whey having no residual rennet activity for use in human foods.

6 Claims, No Drawings

THERMAL DESTABILIZATION OF MICROBIAL RENNET

This invention relates to a method for thermal destabilization of microbial rennet. Rennet is a designation for a milk coagulating enzyme product.

INTRODUCTION

In the production of cheese, the milk is coagulated in order to be able to separate the curds from the whey. Products containing rennin, which is a milk coagulating enzyme isolated from calf stomach, have long been used for this purpose. In the past, the demand for rennet could be met with rennin; but in recent years, several substitutes for rennin have been developed, including notably the microbial rennets from *Mucor miehei* and *Mucor pusillus*. *Mucor miehei* rennet is preferred by the cheese art for its low cost, its low unspecific proteolytic activity and its close resemblance to rennin concerning calcium ion sensitivity. Another of the properties of *Mucor miehei* rennet, one usually considered an advantage for its attribute of long shelf life, is its high thermal stability.

Some of the pasteurized whey is utilized as an additive to whole milk, e.g. in the form of a whey powder, to produce enriched milk, for instance as a baby food. The pasteurized whey resulting from cheese made with *Mucor miehei* rennet may still contain a minor level of rennet activity, due to the high thermal stability of the *Mucor miehei* rennet. Any residual rennet activity in the whey powder is undesirable, since protein coagulation is no longer wanted. Such could take place if the whey powder is used for the production of enriched milk as a baby food. The enriched milk may clot before it enters the stomach of the baby, e.g., in the feeding bottle, thereby causing an obstruction to flow of milk out of the bottle.

It is described in Biochim. Biophys. Acta 271 (1972) 93–101 (W. S. Rickert, Structural and functional determinants of *Mucor miehei* protease, I. Modification of the $NH_2$ terminus and lysine residues by carbamylation) that *Mucor miehei* protease (the active component of *Mucor miehei* rennet) can be carbamylated with potassium cyanate, and that the carbamylated product exhibits a minor degree of thermal destabilization. Practical experiments have shown that the thermal destabilization of the carbamylated enzyme is too small to solve the above-mentioned problem of rennet activity in pasteurized whey.

The object of this invention is to provide an economically-feasible method for thermal destabilization of microbial rennet to such an extent that the disadvantages stemming from the residual microbial rennet activity in pasteurized whey are essentially overcome.

BRIEF STATEMENT OF THE INVENTION

Accordingly, the first aspect of the invention comprises a method for thermal destabilization of microbial rennet by modification of the microbial rennet through acylation in which a microbial rennet is acylated with an active derivative of a carboxylic acid (e.g., an acid anhydride) in an aqueous medium at a pH between about 6 and about 11 and at a temperature between about 0° C. and about 40° C., in a reaction mixture wherein the weight proportion between the acylation agent and the total amount of protein in the enzyme preparation is between 0.01 and 10. Preferably acylation is by a $C_1$-$C_6$ monocarboxylic acid acyl radical.

DISCUSSION OF THE INVENTION

It has been found that the microbial rennet acylated according to the invention is significantly destabilized and that the degree of destabilization suffices to meet the requirements for whey utilization without having detrimental effect on storage stability of the rennet preparation.

The destabilizing result is believed to be surprising, as it appears from Agric. Biol. Chem. 41 (11), 2163–2168 (1977) that acetylation of egg white causes a thermal stabilization.

The rennet activity is measured according to British Standard 3624: 1963 (Method for the determination of the milk coagulating power of rennet).

Since this invention relates to a controlled thermal destabilization of microbial rennet, some elaboration is provided below on techniques to measure thermal stability and to quantify the reduction in thermal stability, the reduction being expressed in °C.

Under ideal conditions, an enzyme may be denatured at a suitable (high) temperature level in such a way that the residual activity of the enzyme decreases as a function of time along an exponential decay curve, i.e., with a well-defined half life, the half life being a function of the temperature (°C.). The half life $T_{\frac{1}{2}}$ can be calculated according to the formula $$T_{\frac{1}{2}} = \frac{(t_2 - t_1) \ln 2}{\ln A_1 - \ln A_2}$$

where $A_1$ is the enzyme activity measured after heating to a specified temperature for the time $t_1$, whereas $A_2$ is the enzyme activity measured after heating to the same specified temperature for the time $t_2$. The half life will be shorter the higher the temperature, everything else being equal. For many enzymes, a change in the pH of the enzyme solution and the ion strength, and the presence of certain salts will influence the half life substantially. Furthermore, chemical derivatization of the enzyme can change the half life considerably. If a chemical derivatization of a particular enzyme causes thermal destabilization of the enzyme, the degree of destabilization is said to be n° C., if the original (non derivatized) enzyme and the derivatized enzyme have the same half life at N°C. and (N−n)°C. respectively.

Normally, the acylation method of this invention is accompanied by activity loss, and it has been found that for economic reasons, the destabilization should not be carried further than an activity loss of around 50%.

In a typical instance, the destabilization of from 3°–5° C. with an activity loss limited to 50% seems to be an appropriate compromise between the above-mentioned conflicting factors.

A preferred embodiment of the method according to the invention comprises acylating with the anhydride of a monocarboxylic acid with between 1 and 6 carbon atoms.

Another preferred embodiment of the method according to the invention comprises destabilization of *Mucor miehei* rennet.

Another preferred embodiment of the method according to the invention comprises the use of an active derivative of acetic acid as the acylating agent, preferably acetic anhydride.

Another preferred embodiment of the method according to the invention comprises the use of propionic anhydride as the acylating agent.

Another preferred embodiment of the method according to the invention comprises acylating with a weight proportion in the reaction mixture between the acylating agent and the total amount of protein in the enzyme preparation of between 0.1 and 1.

As the second aspect, the invention comprises a method for cheese-making wherein the rennet which is modified by acylation according to the present invention is used for milk coagulation. The whey originating from this cheese-making can be used for enriched milk without any problems.

The invention will now be described in more detail by reference to the following examples.

EXAMPLE 1

The starting material is 15 liters of a rennet concentrate prepared as indicated in "2. Pilot plant experiment" in British Pat. No. 1,108,287, only the culture liquid was concentrated to an activity corresponding to a 1% solution of the pure enzyme (Comptes Rendus des Travaux du Laboratoire Carlsberg, Vol. 37, No. 14, 301-325) and 18% NaCl was added to the crude concentrate.

All the following operations were conducted under vigorous agitation.

1. The rennet concentrate was cooled to about 5° C., this temperature being maintained during the following operations. The pH value was adjusted to 10.0 with 0.56 liters of 3.7 N NaOH.
2. The acylation, during which the pH value is kept constant with 3.7 N NaOH addition in a pH-stat, was carried out by adding acetic acid anhydride in small increments consistent with the ability of the pH-stat to keep the pH between 9.7 and 10.0. The addition of acetic anhydride was continued until about half of the enzyme activity was lost. This stage was reached rather suddenly when 51 ml of acetic anhydride was added whereafter the addition of acetic anhydride was interrupted. The acetylation was completed in about 30 minutes.
3. When the acetylation was complete, the pH value was adjusted to 4.7 by addition of about 0.2 liters of 5.2 N HCl. The total volume increase during steps 1-3 was around 5% relative to the volume of the starting material.

With heat treatment of the acetylated enzyme for 30 minutes at 60° C. and at pH 6.0, a half life of 55-85 minutes was found, corresponding to a degree of destabilization of 3° C. A control enzyme material exhibited a half life at 60° C. and pH 6.0 of 300 minutes, and this control exhibited a half life of about 20 minutes at 65° C. and pH 6.0.

EXAMPLE 2

The starting material is a rennet concentrate prepared as indicated in "2. Pilot plant experiment" in British Pat. No. 1,108,287. This concentrate is partially purified by $(NH_4)_2SO_4$ precipitation (40 g/100 ml rennet concentrate), filtration of the precipitate, dissolution of the precipitate in water, and dialysis (ultrafiltration) with membrane DDS (De Danske Sukkerfabrikker) type 800 (this membrane will stop molecules with a molecular weight higher than about 10.000).

This liquid can be called "the partially purified rennet concentrate". 40 ml of the partially purified rennet concentrate containing around 2.7 g enzyme protein and about 1.3 g non-enzyme protein was diluted to 1600 ml with water. The solution was heated to 30° C., and pH was adjusted to pH 8.0 with 1 N NaOH. The acetylation was performed by addition of 100 µl acetic anhydride every tenth minute. pH was currently adjusted to 8.0 with 1 N NaOH. After addition of 1100 µl acetic anhydride, the enzyme activity had dropped to half of the original value.

Then the pH was adjusted to 6.0 with 20% acetic acid, and the solution was ultrafiltrated on a DDS type 800 membrane until the concentrate weighed 40 g. Then 40 g sorbitol was added to the 40 g of concentrate.

A half life of 30-45 minutes at pH 6.0 and 60° C. was determined as described in a previous part of the specification, corresponding to a degree of destabilization of 4° C.

EXAMPLE 3

Three 1 ml portions of the partially purified rennet concentrate from Example 2 were each diluted with 20 ml 0.2 M carbonate buffer and adjusted to pH 9, 10 and 11, respectively. the thus prepared solutions were admixed with 30 µl acetic anhydride at 0° C. with readjustment of pH to 9, 10 and 11 respectively.

After termination of the reaction, the pH was adjusted to 6.0 with 20% acetic acid, and each of the three solutions were diluted with water to a total volume of 25 ml.

The activity yields, evaluated by determination of the rennet activity were as follows:

| pH during acetylation | Activity yield % |
| --- | --- |
| 9 | 55 |
| 10 | 34 |
| 11 | 11 |

Also, the half life values in minutes at pH 6.0 and 60° C. were determined:

| pH during acetylation | Half life, minutes |
| --- | --- |
| 9 | 20 |
| 10 | 13 |
| 11 | 11 |

These half life values correspond to the following destabilization values (°C.):

| pH during acetylation | destabilization, °C. |
| --- | --- |
| 9 | 5 |
| 10 | 5-6 |
| 11 | 6 |

EXAMPLE 4

4 ml of the partially purified rennet concentrate from Example 2 is diluted with 160 ml of water, the pH is adjusted to 8.0 with 1 N NaOH, and the mixture is cooled to 0° C.

Subsequently, the mixed anhydride, formic acetic anhydride, was added with stirring in increments of 10 µl.

After addition of 80 μl of the above mixed anhydride, the rennet activity was reduced to the half of its original value, and no further mixed anhydride was added. At this stage, the pH was adjusted back to about 5.

With heat treatment of the thus formulated rennet at 60° C. and pH 6.00, the half life of the rennet was found to be about 100 minutes, corresponding to a destabilization of about 2° C.

EXAMPLE 5

7 g of commercial Noury rennet 1: 220.000 (batch no. 751 1-22) produced from *Mucor pusillus* was dissolved in 160 ml of water, and pH was adjusted to 8.0 by means of 4 N NaOH.

Then 20 μl portions of acetic anhydride was added at 30° C. to the agitated mixture. After addition of 300 μl of acetic acid, the rennet activity had dropped to 85% of the original rennet activity, and no further anhydride wad added. Then pH was adjusted to about 5.0 by means of 20% acetic anhydride.

When the thus prepared *Mucor pusillus* rennet was heat treated at 55° C. and at pH 6.00, a half life value of around 20 minutes was found. A reference sample of the original (not acetylated) *Mucor pusillus* rennet exhibited a half life of 26–28 minutes under the above temperature and pH conditions.

EXAMPLE 6

1 ml of the partially purified rennet concentrate from Example 2 is dissolved in 20 ml 0.2 M Tris (tris(hydroxymethyl)aminomethane) at pH 7.5. This buffered mixture was cooled to 0° C., and 0.1 g of N-acetyl imidazol was added. After termination of the reaction pH was adjusted to 6.0 by means of 20% acetic acid, and the mixture was diluted to 25 ml. The activity yield was 40%, and the half life at 60° C. and pH 6.00 was 50 minutes, corresponding to a degree of destabilization of 3° C.

EXAMPLE 7

Six 4 ml portions of the partially purified rennet concentrate from Example 2 were diluted with 80 ml 0.2 M bicarbonate buffer at pH 9.0 and the mixture was cooled to 0° C. Then 10 μl portions of the following anhydrides were added:
(1) mixed formic acetic anhydride
(2) acetic anhydride
(3) propionic anhydride
(4) butyric anhydride
(5) isobutyric anhydride
(6) valeric anhydride The addition was continued until the activity of the rennet had dropped to approximately half of the original activity.

Then pH was adjusted to 5.0 by means of 20% acetic acid and the mixture was diluted with water to a total volume of 100 ml.

The main experimental parameters and results are tabulated in the following table:

| Acid corresponding to anhydride used | volume of added anhydride, μl | Activity yield, % | Half life, minutes | Destabilization, °C. |
|---|---|---|---|---|
| Formic, acetic | 180 | 74 | 40 | 4 |
| Acetic | 70 | 62 | 20 | 5 |
| Propionic | 80 | 44 | 12 | 6 |
| Butyric | 20 | 61 | 65 | 3 |
| Isobutyric | 90 | 47 | 17 | 5 |
| Valeric | 100 | 44 | 20 | 5 |

Samples of the thermally destabilized enzymes of the foregoing examples were employed to coagulate milk. The whey was recovered, then pasteurized and thereafter tested for residual rennet activity. In the instance of the enzymes exhibiting destabilization of 3° C. or more, essentially no residual rennet activity was found in the pasteurized whey.

What is claimed is:

1. A method for producing microbial rennet having reduced thermal stability for use in making cheese comprising reacting microbial *Mucor miehei* rennet or *Mucor pusillus* rennet with a monocarboxylic acid acyl radial of between 1 and 6 carbon atoms in an aqueous medium at a pH between about 6 and about 11 and at a temperature between about 0° C. and about 40° C. to produce an acylated microbial rennet having reduced thermal stability of at least about 3° C. and having at least about 50% of the activity before acylating.

2. Method according to claim 1 wherein the source of the monocarboxylic acid acyl radial is acetic anhydride.

3. Method according to claim 1 wherein the source of the monocarboxylic acid acyl radial is propionic anhydride.

4. Method according to claim 1 wherein the weight proportion of the monocarboxylic acid acyl radial to the total amount of microbial rennet protein is between 0.01 and 10.

5. Method according to claim 4 wherein the weight proportion of the monocarboxylic acid acyl radial to the total amount of microbial rennet protein is between 0.1 and 1.

6. A method for making cheese comprising coagulating milk with the rennet modified by acylation according to claim 1 to produce cheese and whey, pasteurizing the whey and using the whey to produce human food.

* * * * *